(12) United States Patent
Bhusarapu et al.

(10) Patent No.: US 8,849,584 B2
(45) Date of Patent: *Sep. 30, 2014

(54) SYSTEMS AND METHODS FOR PARTICLE SIZE DETERMINATION AND CONTROL IN A FLUIDIZED BED REACTOR FOR USE WITH THERMALLY DECOMPOSABLE SILICON-CONTAINING GAS

(75) Inventors: Satish Bhusarapu, Houston, TX (US); Arif Nawaz, Cypress, TX (US); Puneet Gupta, Houston, TX (US); Karthik Balakrishnan, Houston, TX (US)

(73) Assignee: SunEdison, Inc., St. Peters, MO (US)

( * ) Notice: Subject to any disclaimer, the term of this patent is extended or adjusted under 35 U.S.C. 154(b) by 150 days.

This patent is subject to a terminal disclaimer.

(21) Appl. No.: 12/981,074

(22) Filed: Dec. 29, 2010

(65) Prior Publication Data
US 2012/0173165 A1 Jul. 5, 2012

(51) Int. Cl.
*G01N 31/00* (2006.01)
*G01N 15/02* (2006.01)
*G01N 15/12* (2006.01)

(52) U.S. Cl.
CPC ............ *G01N 15/02* (2013.01); *G01N 15/1227* (2013.01)
USPC .............................................. 702/29; 702/55

(58) Field of Classification Search
USPC ..................... 702/29, 55, 27, 28, 45, 47, 50
See application file for complete search history.

(56) References Cited

U.S. PATENT DOCUMENTS

| | | | |
|---|---|---|---|
| 2,981,531 A | 4/1961 | Pyzel | |
| 3,296,319 A | 1/1967 | Bohl et al. | |
| 4,108,968 A | 8/1978 | Jacobs et al. | |
| 4,820,587 A | 4/1989 | Gautreaux et al. | |
| 4,883,687 A | 11/1989 | Gautreaux et al. | |
| 6,849,244 B2 | 2/2005 | Konig et al. | |
| 6,959,618 B1 | 11/2005 | Larsen | |
| 2008/0267834 A1 | 10/2008 | Kim et al. | |
| 2009/0004090 A1 | 1/2009 | Kim et al. | |
| 2010/0044342 A1 | 2/2010 | Kim et al. | |

FOREIGN PATENT DOCUMENTS

| | | |
|---|---|---|
| EP | 0164192 B1 | 12/1985 |
| JP | 2005140745 A | 6/2005 |
| WO | 9961370 A1 | 12/1999 |
| WO | 2010144542 A1 | 12/2010 |

OTHER PUBLICATIONS

Sung Chang Hong et al.; Effects of Particle Size on Pressure Fluctuations along the Axial Direction in a Gas Fluidized Bed; Journal of the Korean Institute of Chemical Engineers; Apr. 1991; pp. 127-133; vol. 29, No. 2; Hwahak Konghad.

Clive E. Davies et al; Particle size monitoring in a fluidized bed using pressure fluctuations; Powder Technology 180; 2008; pp. 307-311; Elsevier B.V.

(Continued)

*Primary Examiner* — Michael Nghiem
*Assistant Examiner* — Eman Alkafawi
(74) *Attorney, Agent, or Firm* — Armstrong Teasdale LLP (57) ABSTRACT

Systems and methods are provided for determining the size of particles within a fluidized bed reactor for use with thermally decomposable silicon-containing gas. The pressure of gas adjacent a gas inlet and adjacent a gas outlet of the reactor are measured with pressure sensors. An algorithm is applied to at least one of the pressure measurements to determine the size of particles within the reactor. The determined size of the particles can be used to control the operation of the reactor.

22 Claims, 5 Drawing Sheets

(56) References Cited

OTHER PUBLICATIONS

C. Sobrino et al; Standard deviation of absolute and differential pressure fluctuations in fluidized beds of group B particles; Chemical Engineering Research and Design 86; 2008; pp. 1236-1242; Elsevier B.V.

Hsiaotao T. Bi; A critical review of the complex pressure fluctuation phenomenon in gas-solids fluidized beds; Chemical Engineering Science 62; 2007; pp. 3473-3493; Elsevier Ltd.

J. Van Der Schaaf et al; Origin, propagation and attenuation of pressure waves in gas-solid fluidized beds; Powder Technology 95; 1998; pp. 220-233; Elsevier Science S.A.

Davis, Clive E. et al; Pressure fluctuations in a fluidized bed: A potential route to the continuous estimation of particle size; IPENZ Transaction, 1997; pp. 12-20; vol. 24, No. 1/EMch.

PCT Invitation to Pay Additional Fees and Search Report mailed on May 2, 2012 regarding PCT/IB2011/055882 filed on Dec. 21, 2011, 4 pages.

Written Opinion issued in related PCT Patent Application PCT/IB2011/055881 filed on Dec. 21, 2011 dated Apr. 5, 2012; 4 pages.

PCT International Search Report and Written Opinion of the International Searching Authority mailed on Aug. 10, 2012 regarding PCT/IB2011/055882 filed on Dec. 21, 2011; 15 pages.

Anonymous; Silo overfill monitoring system: the complete protection for silos and containers; Spec Sheet; Dec. 3, 2006; pp. 1-5.

SYSTEMS AND METHODS FOR PARTICLE SIZE DETERMINATION AND CONTROL IN A FLUIDIZED BED REACTOR FOR USE WITH THERMALLY DECOMPOSABLE SILICON-CONTAINING GAS

BACKGROUND

Polycrystalline silicon is a raw material used to produce many commercial products including, for example, integrated circuits and photovoltaic (i.e., solar) cells. Polycrystalline silicon is typically produced by a chemical vapor deposition mechanism in which silicon is deposited from a thermally decomposable silicon compound onto silicon seed particles in a fluidized bed reactor. These seed particles continuously grow in size until they exit the reactor as polycrystalline silicon particles product (i.e., "granular" polycrystalline silicon). Suitable decomposable silicon compounds include, for example, silane and halosilanes (e.g., trichlorosilane).

Polycrystalline seed particles may be added to the reaction chamber to initiate deposition of silicon. A variety of reactions may take place in the reaction chamber. Silicon deposits from silane onto a silicon particle, resulting in the particle growing in size. As the reaction progresses, silicon particles grow to a desired size and are removed from the reaction chamber and new seed particles are added to the reaction chamber.

Other processes conducted in fluidized bed reactors result in the reduction in size of particles within the reactors. For example, metallurgical-grade silicon and hydrochloric acid may be burned within the reaction chamber to produce trichlorosilane. During this process, the metallurgical-grade silicon particles are eroded and decrease in size as the reaction progresses. These particles are eventually removed once the particles have decreased to a certain size.

Various methods have been used to attempt to estimate the size of particles in the reaction chamber. In one method, the sample particles are removed from the reactor and allowed to cool, after which they are measured. But this method is incapable of real-time measurement of the particle size because there is considerable delay between removal of the particle from the reactor and determination of its size. Another method estimates the size of particles via stoichiometric methods. Still other methods attempt to estimate particle size based on the pressure of gas within the reaction chamber of the fluidized bed reactor. These methods have generally yielded unsatisfactory results.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

One aspect is a system for determining a size of polysilicon particles in a fluidized bed reactor for use with thermally decomposable silicon-containing gas. The system comprises a fluidized bed reactor, a pressure sensor, and a processor. The fluidized bed reactor contains a plurality of polysilicon particles and has an inlet and an outlet. The fluidized bed reactor also has a liner comprising a non-reactive material. The pressure sensor is positioned adjacent the reactor and is configured to measure a gas pressure in at least one of the inlet and the outlet of the reactor. The processor is in communication with the pressure sensor and is configured to determine the size of at least one of the plurality of polysilicon particles in the reactor by use of an algorithm and the measured gas pressure.

Another aspect is a system for determining a diameter of at least one of a plurality of polysilicon particles in a fluidized bed reactor for use with thermally decomposable silicon-containing gas. The fluidized bed reactor has a liner comprising a non-reactive material. The system comprises an inlet pressure sensor and a processor. The inlet pressure sensor is positioned adjacent a gas inlet of the fluidized bed reactor and is configured to measure a gas pressure in the gas inlet of the reactor. The processor is in communication with the first pressure sensor and is configured to determine the diameter of at least one of the plurality of polysilicon particles in the reactor by applying a first algorithm to the measured gas pressure.

Still another aspect is a method for determining a size of at least one of plurality of polysilicon particles in a fluidized bed reactor for use with thermally decomposable silicon-containing gas. The fluidized bed reactor has a liner comprising a non-reactive material. The method comprises measuring a gas pressure in an inlet of the reactor with an inlet pressure sensor. The measured gas pressure in the inlet of the reactor is then communicated to a processor. The processor then determines the size of at least one of the plurality of polysilicon particles in the fluidized bed reactor based at least in part on an algorithm applied to the gas pressure in the inlet of the reactor measured by the inlet pressure sensor.

Yet another aspect is a system for measuring a volume of particles for placement within a fluidized bed reactor for use with thermally decomposable silicon-containing gas. The system comprises a dosing drum for receiving particles from a source, an upper limit sensor, and a lower limit sensor. The upper limit sensor is positioned relative to the dosing drum to detect when the volume of particles in the dosing drum is at a first level. The lower limit sensor is positioned relative to the dosing drum to detect when the volume of particles in the dosing drum is at a second level less than the first level.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

The drawings are not to scale and certain features may be exaggerated for ease of illustration.

DETAILED DESCRIPTION

The systems and methods described herein enable accurate real-time determination of the size of particles within fluidized bed reactors based on the pressure of gas adjacent the gas inlet and/or outlet of the reactor. Previous attempts to estimate the size of particles in the chamber were based on pressure measurements obtained by sensors within the reaction chamber of the reactor. However, such measurements were inaccurate. For example, the pressure sensors often yielded inaccurate readings because the sensors were subject to contact with the particles. This contact was determined to result in fouling of the sensors. Moreover, this contact also resulted in the pressure sensors contaminating the particles as the particles abraded the exposed portions of the pressure sensors.

Figure 1:
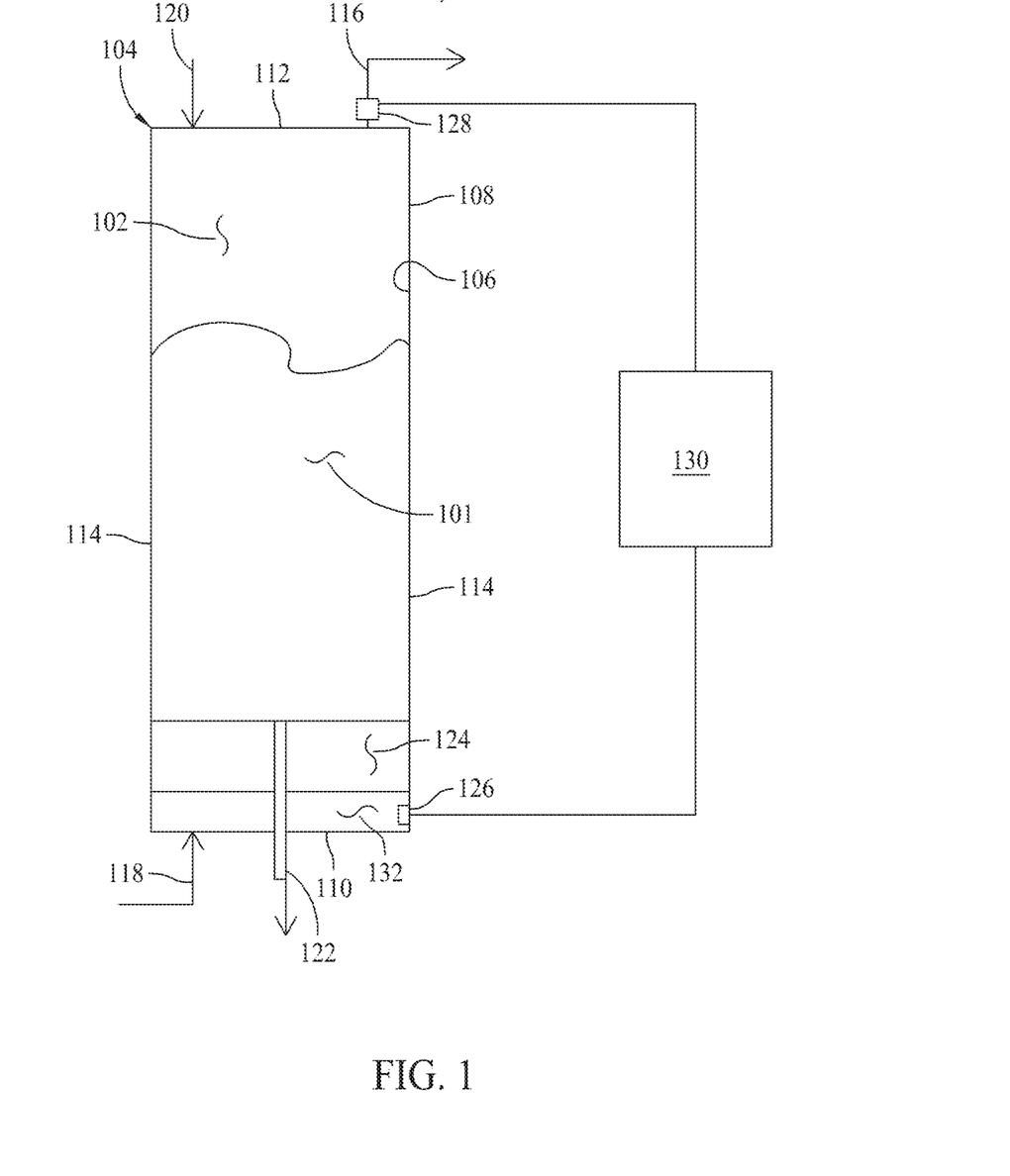
FIG. 1 is a schematic of an exemplary fluidized bed reactor.

Referring initially to FIG. 1, an exemplary fluidized bed reactor is indicated generally at 100. The reactor 100 includes a reaction chamber 102 for receiving a plurality of particles 101. The reaction chamber 102 is defined by a shell 104 having an inner surface 106 and an outer surface 108. The shell 104 may be lined with a liner (not shown) positioned adjacent the inner surface 106 thereof and constructed from a suitably non-reactive material (e.g., quartz or graphite). The shell 104 has a lower end 110 and an opposite upper end 112 connected together by spaced-apart sidewalls 114. In the exemplary embodiment, the shell 104 is cylindrically shaped, although in other embodiments the shell is shaped differently.

The shell 104 has a gas inlet 118 for introducing gas into the reaction chamber 102 and a gas outlet 116 for the removal of gas from the reaction chamber. In the exemplary embodiment, the gases introduced and removed from the reaction chamber 102 may be of any suitable type used in the production of silicon-containing products. For example, the gas may be a thermally decomposable silicon-containing gas or any of the silanes (e.g., monosilane, trichlorosilane, dichlorosilane, or tribromosilane) when the fluidized bed reactor is used to generate granular polysilicon.

The shell 104 also has a particle inlet 120 for the introduction of particles into the reaction chamber 102. A particle outlet 122 in the shell 104 facilitates removal of particles from the reaction chamber 102. In the exemplary embodiment, the particles introduced and removed from the reaction chamber 102 may be of any suitable type used in the production of silicon-containing products. For example, the particles may be granular polysilicon.

As shown in FIG. 1, the gas inlet 118 and the particle outlet 122 are positioned adjacent the lower end 110 of the shell 104, while the gas outlet 116 and particle inlet 120 are positioned adjacent the upper end 112 of the shell. The positions of these components in relation to the shell 104 are exemplary in nature, and may be changed without departing from the scope of the embodiments.

A plate 124 (i.e., a distributor) is positioned within the shell 104 near the lower end 110 of the shell. The plate 124 may be spaced from the lower end 110 of the shell 104 by any suitable distance. The plate 124 is generally porous and has openings formed therein that are sized to permit the passage of gas therethrough while preventing particles from passing through the openings. The plate 124 is constructed from any suitably non-reactive material (e.g., quartz, graphite, or silicon carbide).

The fluidized bed reactor 100 may also include a heat source (not shown) for heating the reaction chamber 102 and the gases and particles contained therein. In the exemplary embodiment, the heat source is an electrical resistance heater positioned adjacent the outer surface 108 of the shell 104.

A first pressure sensor 126 (i.e., an "inlet pressure sensor") is positioned in the shell 104 in a plenum 132 adjacent the gas inlet 118 or in the gas inlet adjacent the plenum. A second pressure sensor 128 (i.e., an "outlet pressure sensor") is positioned in the gas outlet 116. The first pressure sensor 126 is configured to measure the pressure (e.g., pressure amplitude fluctuations or absolute pressure) of gas in the plenum 132 adjacent the gas inlet 118. The pressure of gas in the plenum 132 may be representative of the gas pressure below the plate 124. The second pressure sensor 128 is configured to measure the pressure (e.g., pressure amplitude fluctuations or absolute pressure) of gas in the gas outlet 116. The pressure of gas in the gas outlet 116 may be representative of gas pressure in the reaction chamber 102. Because of their positions, the pressure sensors 126, 128 do not contact the particles 101 disposed within the reaction chamber 102. Accordingly, the pressure sensors 126, 128 do not contaminate these particles 101.

The pressure sensors 126, 128 are connected to a processor 130 by any suitable communication mechanism (e.g., wired and/or wireless communication mechanisms). The processor 130 is a suitable computing device which is operable to perform calculations based at least in part on the pressures measured by the pressure sensors 126, 128 and communicated to the processor. The processor 130 may include various types of computer-readable media, input/output devices, and other components used in computing devices.

Figure 2:
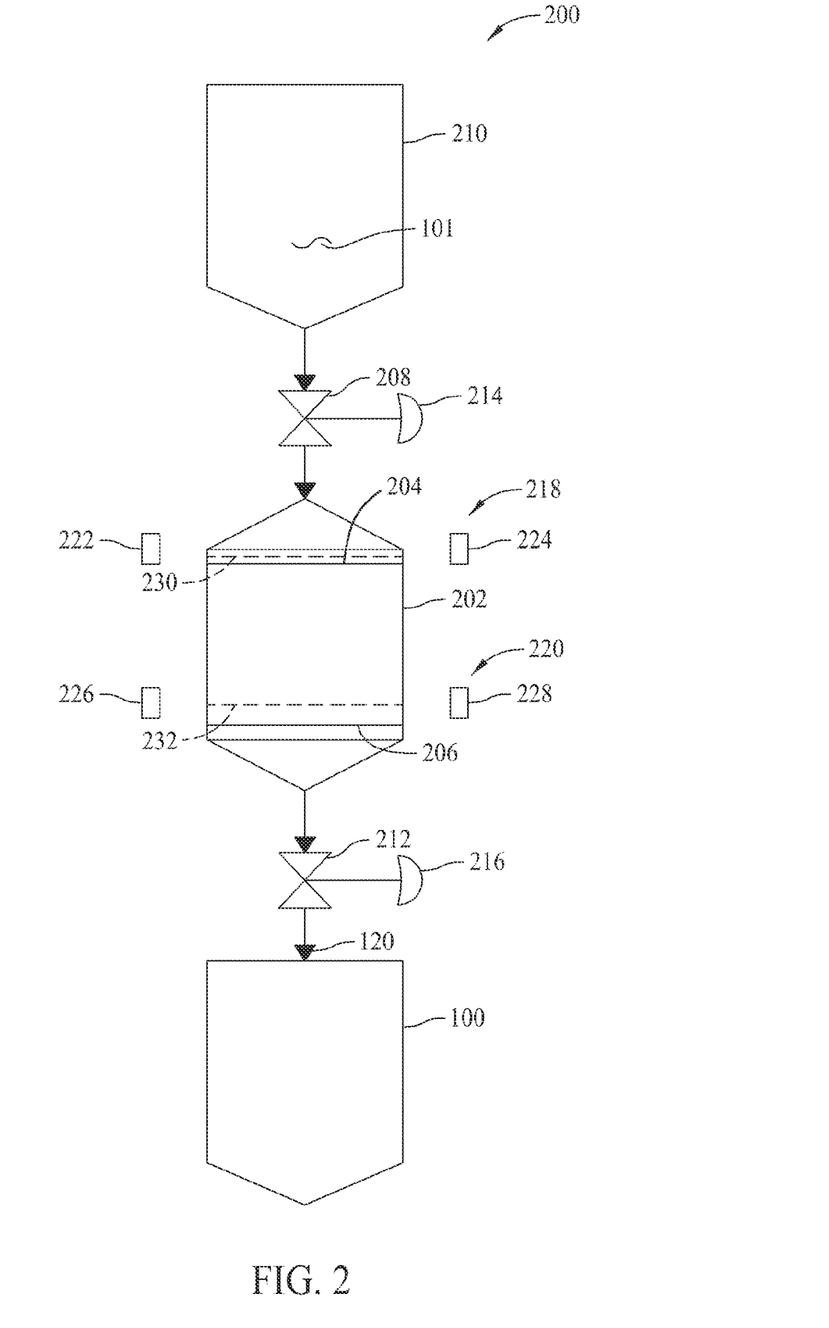
FIG. 2 is a schematic of an exemplary volumetric metering system for use with the fluidized bed reactor of FIG. 1.

A dosing system of embodiment is shown in FIG. 2 and indicated generally at 200. The dosing system 200 is used to meter (i.e., dose) defined volumes of particles 101 for transport into the reaction chamber 102 of the fluidized bed reactor 100 through the particle inlet 120.

The dosing system 200 includes a dosing drum 202 having an upper end 204 and a lower end 206. An inlet valve 208 (i.e., a "first valve") is positioned adjacent the upper end 204 for controlling the flow of particles 101 into the dosing drum 202 from a seed hopper 210. The seed hopper 210 is a container configured for storing bulk volumes of particles 101. An outlet valve 212 (i.e., a "second valve") is positioned adjacent the lower end 206 of the dosing drum 202 and controls the flow of particles 101 from the dosing drum into the particle inlet 120 of the fluidized bed reactor 100.

The valves 208, 212 are any suitable valves that are operable to control the flow of the particles without contaminating the particles. The valves 208, 212 are actuated by respective valve actuators 214, 216 which are in turn controlled by and communicatively coupled to a valve processor (not shown) and/or the processor 130 described above in relation to FIG. 1.

An upper limit sensor 218 is positioned adjacent the upper end 204 of the dosing drum 202 and a lower limit sensor 220 is positioned adjacent the lower end 206 of the dosing drum. In the exemplary embodiment, the limit sensors 218, 220 are nuclear level switches and each include respective emitters 222, 226 and receivers 224, 228. The emitters 222, 226 and receivers 224, 228 are operable to determine when particles are disposed therebetween. The emitters 222, 226 emit radiation therefrom in a linear path and the receivers 224, 228 receive this radiation. When objects (i.e., particles) obstruct the linear path, radiation emitted from the emitters 222, 226 is blocked by the objects which reduces the intensity of radiation received by the receivers 224, 228. The limit sensors 218, 220 are thus capable of indicating when particles are disposed at or above respective levels within the dosing drum 202.

Accordingly, the upper limit sensor 218 is operable to determine when the dosing drum 202 is filled with particles at a level greater than or equal to a first level 230. The lower limit sensor 220 is operable to determine when the dosing drum 202 is filled with particles less than a second level 232.

Figure 3:
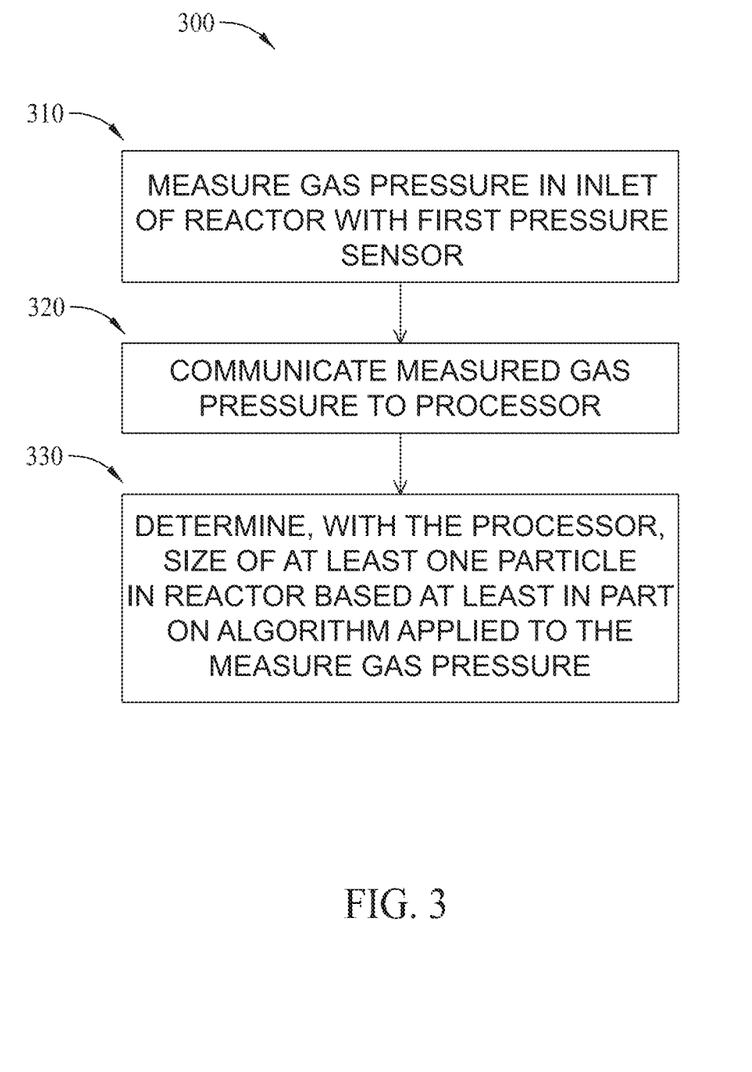
FIG. 3 is a flow diagram showing a method of determining a size of a particle in a fluidized bed reactor.

FIG. 3 shows a method 300 for determining a size of particles in the fluidized bed reactor 100. The method 300 begins in block 310 with measuring the pressure of gas in the gas inlet 118 of the reaction chamber 102 using the first pressure sensor 126. This measured gas pressure is then communicated to the processor 130 in block 320.

The processor 130 then determines the size of the particles in block 330. To make this determination, the processor 130 applies an algorithm or formula to the measured gas pressure. The algorithm or formula used in the exemplary embodiment is reproduced below.

$$\frac{d_{S_i}}{d_{S_k}} = \left[\frac{\mu_i}{\mu_k} \cdot \left(\frac{U_i}{U_{mf_k}} + \frac{\sigma_{p_i} \cdot M_k}{\sigma_{p_k} \cdot M_i} \cdot \left(1 - \frac{U_i}{U_{mf_k}}\right)\right)\right]^{1/2}$$

Subscript i represents the value of a variable at a time $t=t_i$ and subscript k represents the value of a variable at a $t=t_k$. A time of $t_i$ is an initial time, while a time of $t_k$ is a later point in time. The variables in the above equation represent: $d_s$=sauter mean diameter of particles, $\mu$=the viscosity of gas, U=gas superficial velocity, $U_{mf}$=minimum fluidization velocity, $\sigma_p$=amplitude of pressure fluctuations, and M=mass of particles in the reaction chamber. Load cells or other similar mechanisms (not shown) may be used to determine the mass of the particles in the reaction chamber. Given the type of gas, its temperature and pressure, the viscosity of the gas is readily determined based on the kinetic theory of gases. Moreover, other embodiments may use different algorithms to determine size of particles based on the measured pressure. These algorithms may rely in part on the gas pressure measured by both the first pressure sensor 126 and second pressure sensor 128.

Use of the algorithm thus results in the determination of the size (e.g., sauter mean diameter or diameter) of particles in the reaction chamber 120. The determined size may be an average of the size of all the particles in the reaction chamber. This average size may be surface averaged, size averaged, or volume averaged.

In some embodiments, method 300 is used as a feedback control for the operation of the fluidized bed reactor 100. As such, the process performed by the fluidized bed reactor 100 may be altered based on the determined size of the particles. For example, if the method 300 determines the particle diameter is above a threshold level, particles may be removed from the reaction chamber 102 and new particles may be added to the reaction chamber. The rate of removal and/or addition of particles may be increased or decreased as well. In some embodiments, the size of particles added to the reaction chamber 102 may be increased or decreased.

In another instance, if the method 300 determines the particle diameter is below a threshold level, the flow rate of the gas is decreased in order to reduce the rate of particle growth. The flow rate of gas may instead be increased, if necessary, to avoid de-fluidization of the particles within the reaction chamber 102.

In another example, if the method 300 determines the particle diameter is below a threshold level, particles may be removed from the reaction chamber 102 and new particles may be added to the reaction chamber.

In another embodiment, the size of particles within the reaction chamber 102 may be used to measure the performance of the fluidized bed reactor 100 (e.g., rates of conversion/consumption of the decomposing gas and dust production). For example, if the rate of conversion/consumption of the decomposing gas in the reaction chamber 102 decreases, the size of particles within the reaction chamber increase as well. This change in the particle size can be monitored according to the method 300. To compensate for the decrease in the conversion/consumption of the decomposing gas, lower quantities of larger sized particles or larger quantities of smaller sized particles may be added to the reaction chamber 102.

In another instance, an increase in the size of particles within the reaction chamber 102 can indicate a corresponding increase in the rate of dust production. To decrease the rate of dust production, the flow rate of the gas may be altered and/or the size and/or quantity of particles added to the reaction chamber may be changed.

Moreover, in other embodiments the pressure is not measured in the gas inlet 118, and the pressure is measured instead with the second pressure sensor 128 in block 310. The measured pressure in the outlet 116 is then used in the subsequent steps of the method 300. In another embodiment, a differential pressure measured between the gas inlet 118 and the gas outlet 116 is used in block 310. The measured differential pressure is then used in the subsequent steps of the method 300.

The method 300 can continue to be performed at regular intervals in order to determine the size of particles within the reaction chamber 102. For example, method 300 can be performed multiple times per second or method 300 or at any other suitable frequency (e.g., multiple times per minute or hour).

Figure 5:
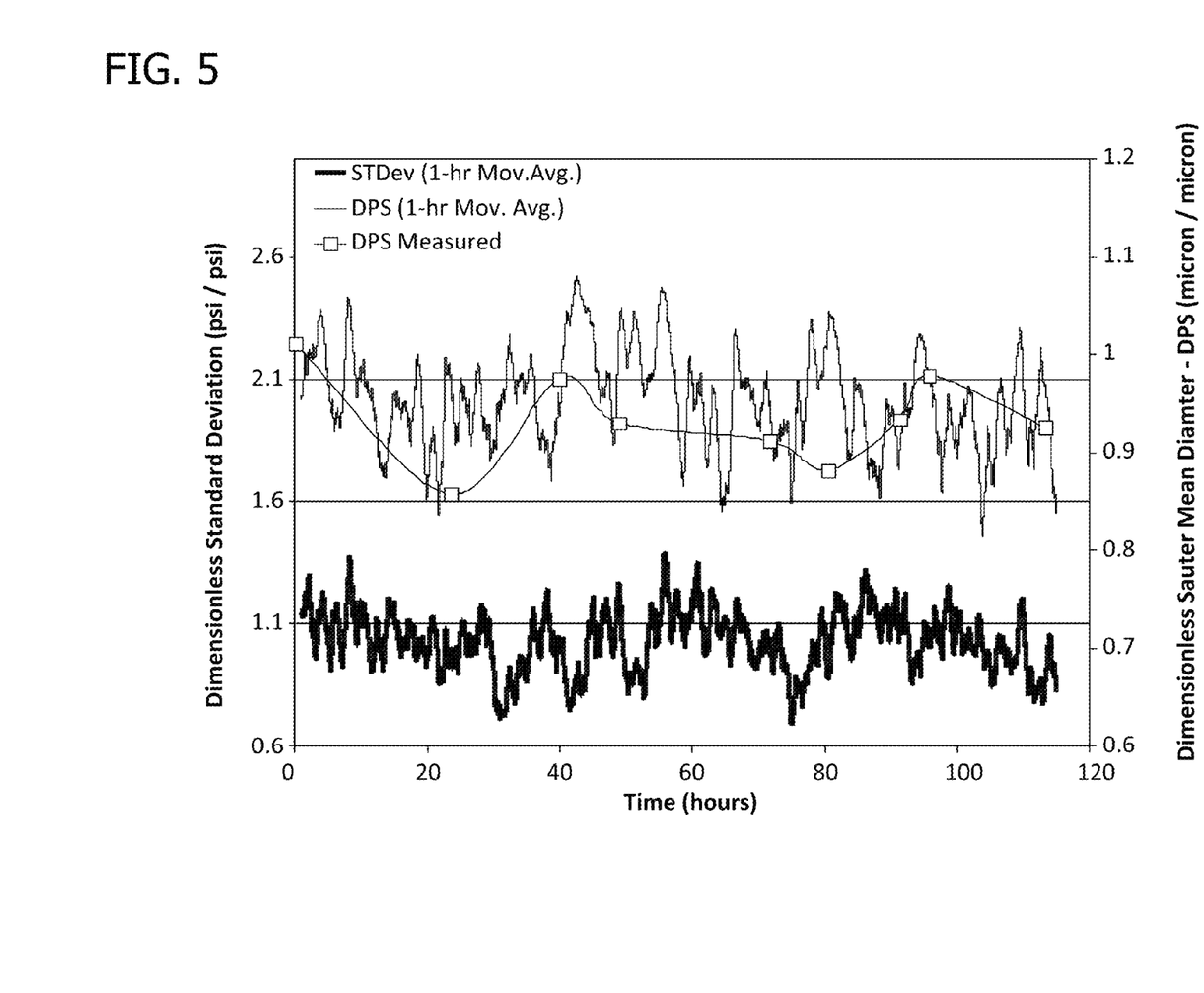
FIG. 5 is a chart showing a comparison of estimated mean particle size according to the method of FIG. 3.

FIG. 5 shows a comparison of estimated mean particle size according to the method 300 with actual physical measurement of particle size.

Figure 4:
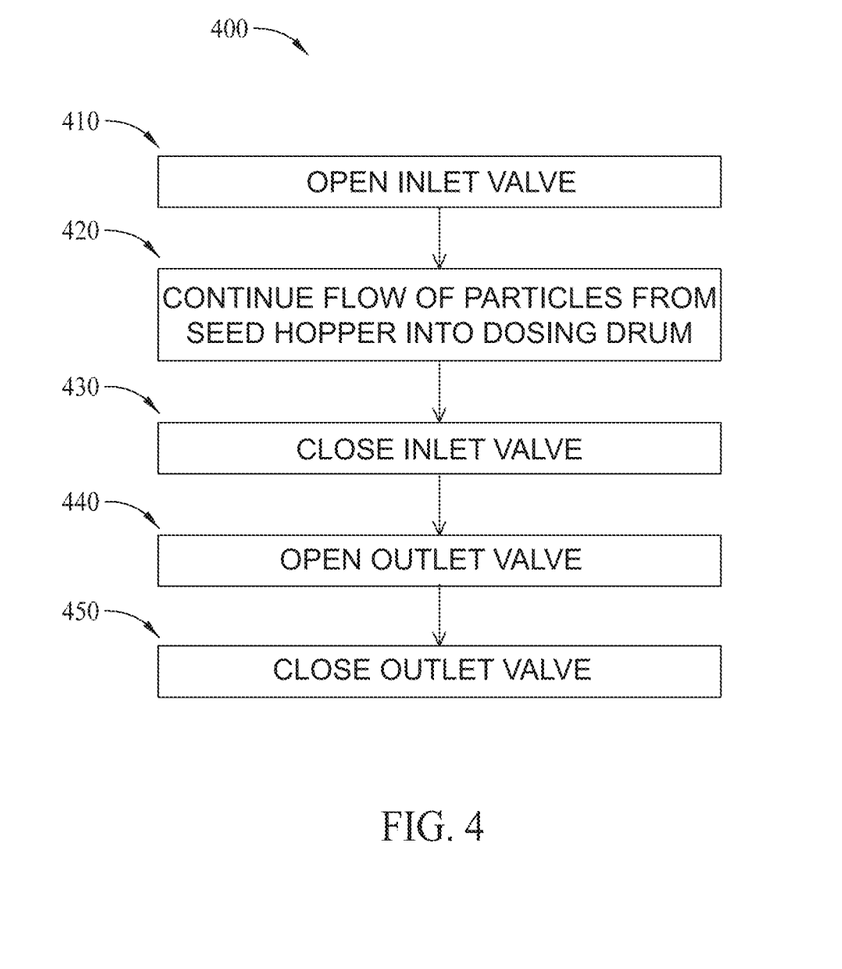
FIG. 4 is a flow diagram showing a method of measuring and dispensing a volume of particles from a dosing drum into the fluidized bed reactor.

FIG. 4 depicts a method 400 of measuring a defined volume of particles with the dosing system 200 of FIG. 2. The defined volume is equal to a volume of the dosing drum 202 between a first level 230 and a second level 232. As described above, the upper limit sensor 218 is positioned to detect when the dosing drum 202 is filled with particles at or above the first level 230. The lower limit sensor 220 is positioned to detect when the dosing drum 202 is filled with particles at or below the second level 232. As the dimensions of the dosing drum 202 and the distance between the first level 230 and the second level 232 are known, the volume of the defined volume is readily determinable.

The outlet valve 212 is closed. Method 400 begins in block 410 with opening the inlet valve 208 such that particles flow from the seed hopper 210, through the inlet valve and into the dosing drum 202.

The flow of particles into the dosing drum 202 continues in block 420 until the level of particles reaches the first level 230. The system 200 uses the upper limit sensor 218 to determine when the particles reach the first level 230. Once the level of particles in the dosing drum 202 reaches the first level 230, the inlet valve 208 is closed in block 430 and the flow of particles into the dosing drum 202 is stopped.

The outlet valve 212 is then opened in block 440 and the defined volume of particles is transported from the dosing drum 202 into the particle inlet 120 of the reaction chamber 102. The dosing drum 202 may be positioned with respect to the particle inlet 120 such that particles are transported to the particle inlet as by gravity or other suitable methods (e.g., pneumatic transport using a pressurized inert gas).

The outlet valve 212 is closed in block 450 when the lower limit sensor 220 determines that the particles are at the second level 232 within the dosing drum 202.

The steps of the method 400 may then be repeated as necessary to transport defined volumes of particles to the particle inlet 120 of the reaction chamber 102. The steps of the method 400 thus provide for the accurate, non-invasive measurement of defined volumes of particles.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description and shown in the accompanying drawings shall be interpreted as illustrative and not in a limiting sense.

What is claimed is:

1. A method for determining a size of at least one of a plurality of polysilicon particles in a fluidized bed reactor for use with thermally decomposable silicon-containing gas, the fluidized bed reactor having a liner comprising a non-reactive material, the method comprising:
    measuring a gas pressure in an inlet of the reactor with an inlet pressure sensor;
    communicating the measured gas pressure in the inlet of the reactor to a processor;
    determining, using the processor, the size of at least one of the plurality of polysilicon particles in the fluidized bed reactor based at least in part on an algorithm applied to the gas pressure in the inlet of the reactor measured by the inlet pressure sensor; and
    controlling the operation of the fluidized bed reactor based at least in part on the determined size of at least one of the plurality of polysilicon particles in the fluidized bed reactor, wherein controlling operation of the fluidized bed reactor includes increasing the flow rate of gas within the fluidized bed reactor when the determined size of at least one of the plurality of polysilicon particles exceeds a threshold level.

2. A method for determining a size of at least one of a plurality of polysilicon particles in a fluidized bed reactor for use with thermally decomposable silicon-containing gas, the fluidized bed reactor having a liner comprising a non-reactive material, the method comprising:
    measuring a gas pressure in an inlet of the reactor with an inlet pressure sensor;
    communicating the measured gas pressure in the inlet of the reactor to a processor;
    determining, using the processor, the size of at least one of the plurality of polysilicon particles in the fluidized bed reactor based at least in part on an algorithm applied to the gas pressure in the inlet of the reactor measured by the inlet pressure sensor; and
    controlling the operation of the fluidized bed reactor based at least in part on the determined size of at least one of the plurality of polysilicon particles in the fluidized bed reactor, wherein controlling operation of the fluidized bed reactor includes decreasing the flow rate of gas within the fluidized bed reactor when the determined size of at least one of the plurality of polysilicon particles falls under a threshold level.

3. A method for determining a size of at least one of a plurality of polysilicon particles in a fluidized bed reactor for use with thermally decomposable silicon-containing gas, the fluidized bed reactor having a liner comprising a non-reactive material, the method comprising:
    measuring a gas pressure in an inlet of the reactor with an inlet pressure sensor;
    communicating the measured gas pressure in the inlet of the reactor to a processor;
    determining, using the processor, the size of at least one of the plurality of polysilicon particles in the fluidized bed reactor based at least in part on an algorithm applied to the gas pressure in the inlet of the reactor measured by the inlet pressure sensor; and
    determining, with the processor, the rate at which the gas is consumed based on the determined size of at least one of the polysilicon particles.

4. The method of claim 1 wherein determining, using the processor, the size of at least one of the plurality of polysilicon particles in the fluidized bed reactor includes determining a diameter of at least one of the plurality of polysilicon particles in the fluidized bed reactor.

5. The method of claim 1 further comprising measuring a gas pressure in an outlet of the reactor with an outlet pressure sensor.

6. The method of claim 5 wherein determining the size of at least one of the plurality of polysilicon particles in the fluidized bed reactor includes applying the algorithm to the gas pressure measured by the outlet pressure sensor.

7. The method of claim 6 wherein determining the size of at least one of the plurality of polysilicon particles in the fluidized bed reactor includes determining, using the processor, a diameter of at least one of the plurality of polysilicon particles in the fluidized bed reactor.

8. The method of claim 1 wherein controlling the operation of the fluidized bed reactor includes one of increasing rate of addition of particles to the fluidized bed reactor and increasing rate of removal of particles from the fluidized bed reactor.

9. The method of claim 1 wherein controlling the operation of the fluidized bed reactor includes one of decreasing rate of addition of particles to the fluidized bed reactor and decreasing rate of removal of particles from the fluidized bed reactor.

10. The method of claim 2 wherein determining the size of at least one of the plurality of polysilicon particles in the fluidized bed reactor includes determining a diameter of at least one of the plurality of polysilicon particles in the fluidized bed reactor.

11. The method of claim 2 further comprising measuring a gas pressure in an outlet of the reactor with an outlet pressure sensor.

12. The method of claim 11 wherein determining the size of at least one of the plurality of polysilicon particles in the fluidized bed reactor includes applying the algorithm to the gas pressure measured by the outlet pressure sensor.

13. The method of claim 12 wherein determining the size of at least one of the plurality of polysilicon particles in the fluidized bed reactor includes determining, using the processor, a diameter of at least one of the plurality of polysilicon particles in the fluidized bed reactor.

14. The method of claim 2 wherein controlling the operation of the fluidized bed reactor includes one of increasing rate of addition of particles to the fluidized bed reactor and increasing rate of removal of particles from the fluidized bed reactor.

15. The method of claim 2 wherein controlling the operation of the fluidized bed reactor includes one of decreasing the rate of addition of particles to the fluidized bed reactor and decreasing rate of removal of particles from the fluidized bed reactor.

16. The method of claim 3 wherein determining the size of at least one of the plurality of polysilicon particles in the fluidized bed reactor includes determining a diameter of at least one of the plurality of polysilicon particles in the fluidized bed reactor.

17. The method of claim 3 further comprising measuring a gas pressure in an outlet of the reactor with an outlet pressure sensor.

18. The method of claim 17 wherein determining the size of at least one of the plurality of polysilicon particles in the fluidized bed reactor includes applying the algorithm to the gas pressure measured by the outlet pressure sensor.

19. The method of claim 18 wherein determining the size of at least one of the plurality of polysilicon particles in the fluidized bed reactor includes determining, using the processor, a diameter of at least one of the plurality of polysilicon particles in the fluidized bed reactor.

20. The method of claim 3 further comprising controlling the operation of the fluidized bed reactor based at least in part on the determined size of at least one of the plurality of polysilicon particles in the fluidized bed reactor.

21. The method of claim 20 wherein controlling the operation of the fluidized bed reactor includes one of increasing rate of addition of particles to the fluidized bed reactor and increasing rate of removal of particles from the fluidized bed reactor.

22. The method of claim 20 wherein controlling the operation of the fluidized bed reactor includes one of decreasing rate of addition of particles to the fluidized bed reactor and decreasing rate of removal of particles from the fluidized bed reactor.

* * * * *